United States Patent [19]

Fournet et al.

[11] Patent Number: 5,541,196
[45] Date of Patent: Jul. 30, 1996

[54] 2-SUBSTITUTED QUINOLINES FOR THE TREATMENT OF LEISHMANIASIS

[75] Inventors: Alain Fournet, Ossages, France; Alcira Angelo Barrios; Victoria Munoz, both of La Paz, Bolivia; Reynald Hocquemiller, Chatenay Malabry Cedex, France; François Roblot, Paris, France; Jean Bruneton, Avrille, France; Pascal Richomme, Angers, France; Jean Charles Gantier, Chatenay Malabry, France

[73] Assignee: Institut Francais de Recherche Scientifique Pour le Developpment en Cooperation (ORSTOM), Paris Cedex, France

[21] Appl. No.: 211,239
[22] PCT Filed: Sep. 29, 1992
[86] PCT No.: PCT/FR92/00903
 § 371 Date: Jun. 9, 1994
 § 102(e) Date: Jun. 9, 1994
[87] PCT Pub. No.: WO93/07125
 PCT Pub. Date: Apr. 15, 1993

[30] Foreign Application Priority Data

Oct. 3, 1991 [FR] France .................. 91/12174

[51] Int. Cl.⁶ .............. C07D 215/06; C07D 215/20; A61K 31/47
[52] U.S. Cl. .............. 514/311; 514/312; 546/153; 546/155; 546/181
[58] Field of Search .............. 546/181, 153, 546/155; 514/34, 3 R

[56] References Cited

U.S. PATENT DOCUMENTS 4,209,519  6/1980  Kinnamon .................. 546/171

OTHER PUBLICATIONS

English Translation of "Aryl–2 et Alkyl . . . ", A. Fournet, Can J Chem, 67(12), pp. 2116–2118, 1989.
A. Fournet, "Aryl–2 et Alkyl–2 Quindléines . . . ", Can J Chem, 67(12) pp. 2116–2118, 1989.

Primary Examiner—C. Warren Ivy
Assistant Examiner—D. Margaret M. Mach
Attorney, Agent, or Firm—Oblon, Spivak, McClelland, Maier, & Neustadt, P.C.

[57] ABSTRACT

Substituted quinolines having formula (1), wherein $R_1$, $R_3$, $R_4$, $R_5$, $R_6$, and $R_7$ each independently represent a hydrogen atom, a linear or branched $C_{1-7}$ alkyl, alkenyl, epoxy-alkyl or mono/polyalcohol group; an amine group or an amide group, an OR group in which R is hydrogen or a $C_{1-7}$ alkyl or alkenyl group or a phenyl group; and $R_2$ is an OR group in which R is as defined above, or a $C_{1-7}$ alkyl alkenyl or epoxyalkyl group, a phenyl, phenol, methylenedioxyphenyl, or dimethoxyphenyl group, or a $C_{1-7}$ alkyl, alkenyl or epoxyalkyl group, a phenyl, phenol, methylenedioxyphenyl, or dimethoxphenyl group or a $C_{1-7}$ alkyl, alkenyl or epoxyalklyl group comprising at least one of the following substituents: a $C_{1-4}$ alkyl or alkenyl group; a phenyl, phenol, dimethylphenyl, dimethoxyphenyl or methylenedioxphenyl group; or an OR group in which R is hydrogen or a $C_{1-4}$ alkyl or alkenyl group; or an NHR group in which R is hydrogen or a $C_{1-4}$ alkyl or alkenyl group; or an amide group; or else $R_2$ and $R_3$ together form a furan ring; and salts and derivatives thereof; are used as drugs, particularly anti-lieshmanials.

14 Claims, 4 Drawing Sheets

2-SUBSTITUTED QUINOLINES FOR THE TREATMENT OF LEISHMANIASIS

This application is a 371 of PCT/FR 92/00903, filed Sep. 29, 1992.

The invention relates to 2-substituted quinolines for the treatment of leishmaniasis.

The term leishmaniasis covers a group of parasitic conditions caused by zooflagellates of the family Trypanosomatidae grouped together under the genus Leishmania.

The Leishmania protozoa parasitize the reticuloendothelial system, causing cutaneous, mucocutaneous or visceral manifestations.

The treatments for leishmaniasis used to date essentially employ antimony salts, especially N-methyl-glucamine antimonate (Glucantime™); 1,5-bis(4-amidinophenoxy) pentane (pentamidine) salts are also used, especially for the treatment of visceral leishmaniasis. Amphotericin B is also used in severe forms resistant to other treatments. These treatments possess the drawback of employing toxic products, which are inconvenient to use since they have to be administered parenterally and exhibit considerable side effects, thereby making them expensive to use, their use being virtually impossible in the absence of hospital facilities and hence economically prohibitive for the majority of the populations of the regions affected by leishmaniasis.

Many studies have been performed with the object of obtaining antileishmanials which are easier to use than those employed at present. To this end, various products which are already known for their anti-infectious activity have been subjected to an evaluation of their biological activity against leishmanias: these comprise, for example, antifungals, especially ketoconazole and its derivatives, or antibiotics such as rifampicin.

Antiparasitics, especially antimalarials, have also been tested: there may be mentioned, for example, primaquine [HANSON et al., Int. J. Parasitol., 7 443–447, (1977); BEVERIDGE et al., Trans. R. Soc. Trop. Med. Hyg., 74, 43–51, (1980)] or derivatives of the latter [SHETTY et al., J. Med. Chem. 21, 995–998, (1978)], and other 8-aminoquinoline derivatives such as lepidines[KINNAMON et al., Am. J. Trop. Med. Hyg., 27, 751–757, (1977)]; these different compounds have shown greater or lesser antileishmanial activity in vitro, and some of them also possess significant activity in vivo when they are administered parenterally; quinine and chloroquine have also been tested, but proved weakly active in vitro and inactive in vivo [MATTOCK and PETERS., Ann. Trop. Med. Parasitol., 69, 359–371 (1975); PETERS et al., Ann. Trop. Med. Parasitol., 74, 289–298 (1980); PETERS et al., Ann. Trap. Med. Parasitol., 74 321–335 (1980)].

Recently, BAUMANN et al. [Antimicrob. Agents Chemoter., 35, 1403–1407, (1991)] have shown the efficacy in vivo via the parenteral route and via the oral route of a polyamide analog on *L.donovani*; this polyamine analog is the only product to date for which significant activity via the oral route has been demonstrated.

Different plant-based treatments are also used by the indigenous populations in the regions where leishmaniasis is endemic [FOURNET et al. J. Ethnopharmacol., 24, 337 (1988)]. These plants are, in general, used in local applications, on the lesions.

The plants used in this way are more or less well identified from a botanical standpoint, and no proper evaluation of their true efficacy has been performed to date.

The inventors undertook a study of different plants recommended in the traditional pharmacopeia of the Indian populations of South America for the treatment of leishmaniasis. In this way, they came to demonstrate the effective action on Leishmania of extracts of *Galipea longiflora* Krause.

*Galipea longiflora* [KRAUSE, Notizbl. K. Bot. Gart. Berlin, 6, 143, (1914)] belongs to the genus Galipea of the family Rutaceae. It is a shrub 10 to 15 meters in height present in Bolivia and in the regions bordering on Brazil to the north east of Bolivia. Its fresh bark, reduced to paste, is used in the local traditional medicine in poultices for the topical treatment of cutaneous lesions caused by *Leishmania braziliensis*, as well as in a decoction for the treatment of amebic dysentery.

Some species of the genus Galipea have been subjected to chemical studies the species in question are *Galipea officinalis*Hancock [MESTER, Fitoterapia, 44, 123, (1973)], and recently *Galipea bracteata* [VIERA and LUBO, Phytochem. 29, 813, (1990)] and *Galipea longiflora* [FOURNET et al., Can. J. Chem., 67 2116 (1989)]. Although these studies have made it possible to demonstrate a large number of constituents of these plants, including quinoline alkaloids, none of these constituents has been described as possessing antileishmanial activity.

Nevertheless, the inventors continued their investigations on *Galipea longiflora*, with the object of identifying substances responsible for the antileishmanial activity.

Their work has now led to the demonstration of different quinoline alkaloids, some of which exhibit an antileishmanial activity comparable to or greater than that of N-methylglucamine antimonate, taken as reference product.

The subject of the present invention is substituted quinolines of general formula (I)

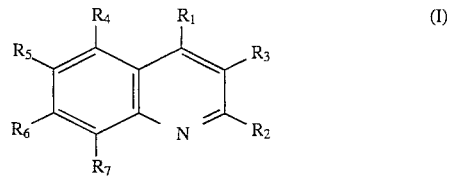

in which $R_1$, $R_3$, $R_4$, $R_5$, $R_6$ and $R_7$ each represent, independently, a hydrogen atom, a linear or branched $C_1$ to $C_7$ alkyl alkenyl, epoxyalkyl or mono- or polyhydric alcohol group, an amine group or an amide group, a group OR in which R represents hydrogen or a $C_{1-7}$ alkyl or alkenyl group or a phenyl group; and $R_2$ represents:

a group OR in which R has the same meaning as above, or alternatively a $C_1$ to $C_7$ alkyl, alkenyl or epoxyalkyl group, a phenyl group, a phenol, methylenedioxyphenyl or dimethoxyphenyl group, or alternatively a $C_{1-7}$ alkyl, alkenyl or epoxyalkyl group bearing at least one of the following substituents: a $C_{1-4}$ alkyl or alkenyl group; a phenyl, phenol, dimethylphenyl, dimethoxyphenyl or methylenedioxyphenyl group; or a group OR' in which R' represents hydrogen or a $C_{1-4}$ alkyl or alkenyl group; or a group NHR" in which R" represents hydrogen or a $C_{1-4}$ alkyl or alkenyl group; or an amide group, or alternatively $R_2$ and $R_3$ together form a furan ring; as well as the salts and the derivatives of said quinolines, for use as medicinal products.

According to a preferred embodiment of the present invention, $R_3$, $R_4$ and $R_5$ represent a hydrogen atom and $R_1$, $R_6$ and $R_7$ represent a hydrogen atom or a methoxy group.

According to another preferred embodiment of the present invention, $R_2$ is an ethyl, ethylene or epoxyethyl group bearing at least one of the following substituents:

a $C_{1-4}$ alkyl or alkenyl group, or a group OR' in which R' represents hydrogen or a $C_{1-4}$ alkyl or alkenyl group, a phenyl, phenol, dimethylphenyl, dimethoxyphenyl or methylenedioxyphenyl group, an amide or amine group.

Said quinolines may be extracted from a plant of the genus Galipea. They may also be obtained by chemical synthesis, according to any process known per se, for example that described by ISHIKURA et al. [Heterocycles, 23, 2375 (1985)].

The invention encompasses, for use as a medicinal product, both new 2-substituted quinolines and 2-substituted quinolines which are known per se but for which no therapeutic, and especially antileishmanial, property was known or suggested hitherto.

Preferred quinolines are those which are 2-substituted with a saturated or unsaturated and substituted or unsubstituted chain containing 3 carbon atoms; in this context, the invention relates especially to 4-methoxy-2-n-propylquinoline, assigned the name chimanine A, and 2-(1',2'-trans-epoxypropyl)quinoline, assigned the name chimanine D, which are new, as well as 2-n-propylquinoline and 2-propenylquinoline, which are already known [VIEIRA and KUBO; ISHIKURA et al., publications cited above], but whose antileishmanial properties were not known.

The antileishmanial quinolines according to the invention are active both against the leishmanias responsible for the cutaneous and mucocutaneous leishmaniasis (for example *Leishmania amazonensis, Leishmania venezuelensis,* and the like) and against those responsible for visceral leishmaniasis (*Leishmania donovani, Leishmania infantum*); they can be used in human medicine or in veterinary medicine; they are, in addition, active via the oral route.

The subject of the present invention is, in addition, pharmaceutical compositions for the treatment of leishmaniasis, which comprise as active principle at least one quinoline as defined above.

According to a preferred embodiment of the present invention, said pharmaceutical compositions are formulated for oral administration.

A better understanding of the present invention will be gained from the additional description which follows, which relates to examples of preparation of quinolines according to the invention and of demonstration of their antileishmanial activity.

It is, however, self-evident that these examples are given only by way of illustration of the subject of the invention, of which they in no way constitute a limitation.

EXAMPLE 1

OBTAINING ANTILEISHMANIAL QUINOLINES FROM *GALIPEA LONGIFLORA*

The quinolines were obtained from different organs (leaves, root and trunk bark) of *Galipea longiflora*, dried and ground, by extraction with petroleum ether followed by extraction with chloroform, and were purified by chromatography on a column of silica H (MERCK) (elution with an 80:20 hexane/ethyl acetate mixture).

The respective chemical names of the different alkaloids extracted and which possess activity in vitro against leishmanias are as follows:

Alkaloid I: 2-phenylquinoline

Alkaloid II: 2-n-pentylquinoline

Alkaloid III: 2-n-propylquinoline

Alkaloid IV: 4-methoxy-2-phenylquinoline

Alkaloid V: 2-(3',4'-methylenedioxyphenethyl)quinoline

Alkaloid VI: 4-methoxy-2-n-pentylquinoline

Alkaloid VII: 4-methoxy-2-n-propylquinoline or chimanine A

Alkaloid VIII: 4-methoxy-2-(3',4'-methylenedioxyphenethyl)quinoline or cusparine Alkaloid IX: 2-(3',4'-dimethoxyphenethyl)quinoline Alkaloid X: 4,7,8-trimethoxy-(2,3-furo)quinoline or chimanine Alkaloid XI: 2-propenylquinoline or chimanine B Alkaloid XII: 2-(1',2'-trans-epoxypropyl)quinoline or chimanine D Alkaloid XIII: 4-methoxy-2-propenylquinoline or chimanine C.

I-SYNTHESIS OF 2-SUBSTITUTED QUINOLINES

EXAMPLE 2

PREPARATION OF 2-(HYDROXYPROPYL)QUINOLINE AND 2-PROPENYLQUINOLINE FROM 2-METHYLQUINOLINE

1) Preparation of 2-(hydroxypropyl)quinoline 110 ml of 1.6 M n-butyllithium in hexane (>0.16 mol) together with 100 ml of anhydrous ether are introduced into a three-necked flask placed under nitrogen, and cooled to 0° C. 21.65 ml of 2-methylquinoline (0.16 mol) are added dropwise and with stirring using a dropping funnel. The solution is left stirring for 20 minutes at room temperature before being cooled to −30° C. and adding 13.54 ml of acetaldehyde (0.24 mol) via the funnel. The funnel is rinsed with 30 ml of anhydrous ether and the solution is allowed to return to 0° C.

After 3 hours, the reaction proceeding no further, the mixture is hydrolyzed with saturated ammonium chloride solution. The product is extracted three times with ether. The organic phase is dried over sodium sulfate and evaporated under reduced pressure. The residue obtained is chromatographed on a silica column (heptane/ethyl acetate, 4:6) to yield 7.5 g of 2-(hydroxypropyl)quinoline and 14.1 g of the starting quinoline. (Yld=25%).

2) Preparation of 2-propenylquinoline

2-Propenylquinoline is obtained from 2-(hydroxypropyl)quinoline by dehydration in acetic acid in the presence of acetic anhydride.

In a round-bottomed flask surmounted by a condenser and a calcium chloride guard tube, 468 mg of 2-(hydroxypropyl)quinoline are dissolved in a mixture of 0.5 ml (5 mmol) of acetic anhydride and 0.5 ml (8.3 mmol) of glacial acetic acid.

The solution is stirred over a steam bath for 45 min. A little water and sodium carbonate are added and the mixture is then neutralized with 1 M sodium hydroxide solution. The aqueous phase is extracted three times with ether. The organic phase is dried and then taken to dryness by evaporation under reduced pressure. The residue obtained is chromatographed on silica (hexane/ethyl acetate/dichloromethane, 20:4:76), and 250 mg of 2-propenylquinoline are obtained (Yld=54%).

EXAMPLE 3

PREPARATION OF 2-(2-HYDROXY-2-PHENYLETHYL)QUINOLINE AND 2-STRYLQUINOLINE

The method used is that of SKIDMORE and TIDD[The Quinoline series, Part I, 1641–1645, (1959)]. 5.3 ml of 2-methylquinoline (0.039 mol) and 3.56 ml of benzaldehyde 0.035 mol) are mixed with a little benzoic acid. The mixture is stirred at room temperature and the product is then left to crystallize for several weeks. The solution is filtered through sintered glass and the filter is rinsed with cold ethanol. The crystals remaining on the sintered glass are recrystallized in ethanol and then placed in a heating desiccator. 1.53 g of 2-(2-hydroxy-2phenylethyl) quinoline are thereby obtained (Yld=24%). The filtrates are combined, the solvent is evaporated off therefrom and the products are then deposited on a silica column. 3.66 g of 2-methylquinoline and 1.9 g of 2-styrylquinoline are then obtained (Yld=18%). 69% of the starting 2-methylquinoline is recovered.

Larger amounts of 2-styrylquinoline are obtained by catalyzing the dehydration of 2-(2-hydroxy-2-phenylethyl) quinoline with para-toluenesulfonic acid, and removing the water by azeotropic distillation.

EXAMPLE 4

PREPARATION OF 2-(1',2'-TRANS-EPOXYPROPYL)QUINOLINE 0.42 g of N-bromosuccinimide (2.35 mmol) is added in small portions to a solution of 330 mg of 2-propenylquinoline (1.96 mmol) in 12 ml of dioxane and 5 ml of water. After stirring for 9 hours at room temperature, the reaction mixture is poured into water and extracted with ether. The organic phase is dried over sodium sulfate and the ether is evaporated off.

To the two intermediate regioisomers thereby obtained, 10 ml of isopropanol and a few drops of phenol-phthalein are added, and the mixture is titrated with 1 M sodium hydroxide solution. The solution is thereafter diluted with 10 ml of water, and a precipitate then forms which is extracted 3 times with ether. The residue obtained after the ether phase has been passed over sodium sulfate and the solvent has been evaporated off is deposited on a silica column (hexane/ ethyl acetate, 9:1). 160 mg of 2-(1',2'-trans-epoxypropyl)quinoline (racemic mixture; Yld=44%) and 80 mg (Yld =22%) of 2-(dibromopropyl) quinoline are obtained.

EXAMPLE 5

PREPARATION OF 2-(1',2'-TRANS-EPOXYPHENETHYL)QUINOLINE FROM 2-STYRYL-QUINOLINE

The same procedure as in Example 4 is followed, using 1.04 g of 2-styrylquinoline (4.5 mmol), 0.96 of N-bromosuccinimide (5.4 mmol) in 38 ml of dioxane and 16 ml of water. After chromatography on silica (hexane/ ethyl acetate, 8:2), 790 mg (54%) of 1-phenyl-1-bromo-2(2-quinolyl) ethanol and 70 mg (4%) of 2-(1,2 -dibromophenethyl) quinoline are obtained.

640 mg of 1-phenyl-1-bromo-2-(2-quinolyl)ethanol (2.42 mmol) undergo the second part of the treatment. After purification on a silica column (hexane/ethyl acetate, 8:2), 510 mg of 2-(1',2'-trans-epoxyphenethyl) quinoline are obtained.

II-BIOLOGICAL ACTIVITY OF THE QUINOLINE ALKALOIDS ACCORDING TO THE INVENTION

EXAMPLE 6

BIOLOGICAL ACTIVITY IN VITRO

The biological tests were performed on promastigotes of *Leishmania braziliensis* (strains M 2903 or M 2904), Leishmania amazonensis (strains PH 8 or H 142) and *Leishmania donovani* (strain M 2682) and on the epimastigotes of *Trypanosoma cruzi* (strains Tulahuen, C 8CL1 and Tehuentepec).

a) In vitro culture of Leishmania at the promastigote stage

The promastigote form of the different strains of Leishmania ssp is maintained in culture in vitro by successive subculturings (every 7 to 15 days depending on the strain) in 25 ml "Corning" type culture dishes or in culture tubes.

To obtain better growth of the parasites, 2 ml of liquid NNN culture medium (Novy, MacNeal, Nicoll) are added into a dish, followed by 50 μ of culture medium containing approximately $8 \times 10^6$ parasites/ml, equivalent to approximately 400,000 parasites per dish. This inoculum is removed to a tube in which the presence of promastigotes has been observed under a microscope. These parasites are in large part young forms. They are left 48 hours in an incubator at 28° C., and 2 ml of NNN medium are added again.

b) In vitro culture of *Trypanosoma cruzi* at the epimastigote stage

The epimastigote form of the different strains of *Trypanosoma cruzi* is maintained in culture in vitro by successive subculturings every week approximately in 25-ml "Corning" culture dishes or in culture tubes.

The parasites are cultured in complete LIT liquid medium (Yager's Liver Infusion Tryptose) at pH 7.2, supplemented with 1% of fetal calf serum (FCS) inactivated at 56° C. for 30 minutes and a solution of antibiotics containing 0.25 mg/ml of streptomycin and 250 U/ml of penicillin.

c) In vitro biological tests

The biological tests are carried out in sterile "Limbro" or "Falcon" type 96-flat-bottomed-well microplates with lid. The capacity of each well is approximately 0.35 ml.

The solvent employed for dissolving the plant extracts or purified alkaloids to be tested is, in general, DMSO (dimethyl sulfoxide). Before undertaking the tests with the plant extracts or alkaloids, the cytotoxicity of DMSO was evaluated. It is apparent that this solvent employed at concentrations not exceeding 0.5% has no effect on the growth of the parasites.

2 mg of plant extract or of purified quinoline are dissolved in 40 μ of DMSO with agitation (Vortex). To this preparation, the necessary amount of NNN medium (or alternatively of LIT medium in the case of *T. cruzi*) for obtaining the desired concentration is added. The tests designed to verify the activity of the extracts after each purification step are performed at a final concentration of 100 μg.ml$^{-1}$ of plant extract.

If the extract is active at a concentration of 100 μg-ml$^{-1}$, the minimum dose which completely inhibits the parasites is determined by preparing solutions at a concentration of 50 μg, 25 μg, 5 μg and 1 μg.ml$^{-1}$, as required.

The parasites are taken in the exponential growth phase. Counting of the parasites is generally performed by diluting the inoculum 10 times. An aliquot of the solution containing the parasites is sampled and then counted using a Thoma cell.

After this count, the parasite concentration is adjusted to $10^6$ parasites per ml using a micropipette, and 100 µl of parasites are then deposited in each well of the microplate, that is to say the equivalent of 100,000 parasites. The same amount of culture medium (100 µl) containing the plant extract at a concentration of 200 µg.ml$^{-1}$ is then added. Each plant extract is tested in triplicate on each strain of parasites and at each concentration. Into the control wells containing the parasites alone, 100 µl of medium without parasite are added in order to make the volume to 200 µl. Wells including parasites alone are also prepared with the culture medium containing the same amount of DMSO (40 µl) as used for dissolving the plant extracts, in order to check for a possible solvent effect.

The plates are closed with a lid which has previously been flamed in order to avoid contamination, and are placed in an incubator at 28° C. for 48 h or 72 h according to the requirements of the experiment. After this storage in the incubator, the plates are examined under an inverted microscope. Each well is observed, comparing it with the control culture wells.

After 48 or 72 hours of contact with the plant extracts, the changes which have occurred are observed under a microscope, and the concentration which causes complete lysis of the parasites is noted.

d) Results

Alkaloids I, II, V, VI, VIII, IX and X cause complete lysis of the cultures of parasites (Leishmania and Trypanosoma) at a concentration of 100 µg/ml. Alkaloids III, IV and XII have the same action at a dose of 50 µg/ml, and alkaloid XI at a dose of 25 µg/ml.

EXAMPLE 7

ACTIVITY IN VIVO OF THE ALKALOIDS ACCORDING TO THE INVENTION AGAINST *L. AMAZONIENSIS* AND *L. VENEZUELENSIS*

MEASUREMENT OF THE TOXICITY OF THE PRODUCTS ($LD_{50}$)

Before performing the tests on mice, the degree of toxicity of the quinolines was determined.

The method chosen is measurement of the 50% lethal dose ($LD_{50}$) with a single dose. The $LD_{50}$ corresponds to the dose capable of killing, under specified conditions, one half of the animals subjected to experiment in a single animal species. Since the curve representing mortality as a function of the logarithm of the doses is assumed to be a straight line between the two doses flanking the $LD_{50}$, ) the latter is calculated by interpolation as follows:

$$\log LD_{50} = \log \cdot B + \frac{0.5 - N}{M - N} \log \gamma$$

B=dose immediately below the $LD_{50}$

N=mortality caused by the dose B (percentage expressed as a decimal fraction relative to 1)

M=mortality caused by the dose immediately above the $LD_{50}$ (percentage expressed as a decimal fraction of 1)

γ=common ratio of the progression.

The following working conditions were chosen:

Experimental animals: BALB/c mice,

Number of animals per concentration of product: 6 mice of the same sex, same weight and same age, Experimental doses in mg.kg$^1$: 400, 200, 100, 50, 25, 12.5 (common ratio of the progression 2), Product inoculation route: intraperitoneally, Calculation of the $LD_{50}$: at time 0 and after 24 h, 48 h and 72 h.

All the quinolines tested have an $LD_{50}$ of greater than 400 mg/kg, 72h after inoculation of the products. For the remainder o f the experiment, the dose of 100 mg/kg was employed.

1. Experimental protocol

Each experimental group comprises 10 BALB/c mice of the same sex, same weight and same age. For each experiment, several experimental groups are formed:

a parasite control group (Con.) not receiving an$_y$ treatment a parasite control group receiving throughout the treatment a PBS solution (Con.+PBS), the medium which contains the parasites a group receiving as treatment the reference medicinal product, N-methylglucamine antimonate or Glucantime$^R$ (marketed by Specia France) on the basis of 200 mg.kg$^{-1}$ a group of mice treated with a quinoline isolated from *Galipea longiflora* or obtained by synthesis as described in one of Examples 1 to 4, at a concentration of 100 mg/kg.

2. Mice

The experimental animals are approximately 8-week-old male or female BALB/c mice weighing 18–24 g. BALB/c mice were chosen on account of their great sensitivity to Leishmania spp and to *Trypanosoma cruzi*.

3. Maintenance of the parasite

At the start, the amastigote forms of *L. amazonenzis* were obtained by subcutaneous inoculation of promastigotes of the strains IFLA/BR/67/PH8 or MHOM/GF/84/CAY H-142, or of *L. venezuelensis* (Ref. MHOM/VE/74/PM-H3), in the dorsal side of the hind feet of hamsters (Charles Rivers, USA) weighing 120–130 grams. Granulomas appear after 8 to 12 weeks, depending on the virulence of the strain.

For the remainder of the experiment, the hamsters are infected with the amastigote forms recovered in the granulomas. By this method the granulomas develop more rapidly.

4. Preparation of the parasites and infection

To obtain amastigotes, a hamster displaying a non-ulcerated granuloma of sufficient size is chosen. The animal is killed with chloroform. The hind foot infected with the parasites is cleaned with alcoholic iodine tincture and then with ethanol at 70°. Using a sterile 14 forceps and sterile scalpel, the granuloma is resected. The granuloma is then chopped over a mortar containing sterile sand and 5 ml of 0.9% sodium chloride. The whole is homogenized using a pestle, and the suspension is collected with a pipette and centrifuged at 2000 rpm for 10 min at 4° C. Three layers are obtained, the supernatant containing the debris of parasites and cells, the bottom with the sand and the large debris of the granuloma, and the intermediate layer composed of parasites and red cells. This intermediate layer is withdrawn and placed in a tube, rinsed with 0.9% sodium chloride and centrifuged again to separate the red cells from the parasites, which take the form of a white layer.

The parasites are taken up in an MEM (minimum essential medium) nutrient medium with 10% of FCS (fetal calf serum), 2% of L-glutamine and 1% of antibiotics. They are diluted and counted using a Thoma cell. One granuloma enables approximately $10^8$ parasites to be obtained. The concentration is adjusted to $10^6$ parasites per ml. The parasites thereby obtained are used for infecting the BALB/c mice and for carrying out the in vivo biological tests of the products isolated from plants. This technique of isolation of the parasites is the same for all the Leishmania strains used for this work [*L. amazonensis* PH8 and H-142) and *L. venezuelensis* (H-3), Bonfante-Garrido, 1983)].

5. Infection with *Leishmaia amazonensis* and *L. venezuelensis*.

Mice are infected with amastigotes of *Leishmania venezuelensis*, of the reference strains IFLA/BR/67/PH8 or MHOM/GF/84 CAY H 142, or of *Leishmania venezuelensis* (reference MHOM/VE/74/PM-H3) originating from Barquisimeto, Venezuela (host:man), subcutaneously in the ventral pad of the right hind foot, the left foot serving as control.

The amount of amastigotes inoculated is $10^e$ in 0.2 ml of PBS for the *Leishmania amazonensis* (PH 8) and *Leishmania venezuelensis* (H-3) strains, and $3 \times 10^6$ amastigotes for the *Leishmania amazonensis* (H-142) strain in the same volume of PBS. This parasite concentration was previously determined by tests at different parasite concentrations.

6. Treatment with the active principles

Treatments begin 24 hours after the inoculation of amastigotes of Leishmania spp and last for 14 consecutive days.

N-Methyl glucamine antimonate is dissolved in distilled water and injected at a dose of 200 mg.kg$^{-1}$ in 200 µl. The test quinoline is solubilized in 40 ml of polysorbate (Tween 80, Prolabo) supplemented with PBS medium to obtain the desired concentration. 200 µl of the solution obtained are then inoculated subcutaneously in the dorsum. The concentration of the product depends on its toxicity. Few problems were encountered during injection of the products. In all the mice treated, a local inflammation was observed at the injection site, which generally disappears when the treatment is suspended.

Tests of local inoculation of the medicinal products in the infected foot were also carried out. The mice are infected in the manner described above, but the treatment is performed 14 days after parasitic infection, and in a single injection into the plantar pad of the hind foot infected with the parasites.

For these local inoculation tests, the concentrations of medicinal products administered are multiplied by two. The medicinal products are prepared in the same manner as for the systemic treatments.

7. Parameters studied

The diameters of the lesions of the infected foot and of the control foot are measured every week for 8 weeks, beginning the first measurements 48 hours before inoculation of the parasites, using a micrometer graduated in 1/10mm. Calculation of the difference between the two measurements gives the thickness of the lesion, or leishmanian index (L.I.).

The results are expressed by calculation of the arithmetic mean of the leishmanial indices, and calculation of the confidence interval of the observed mean, at the risk equal to 5% which is calculated with the following formula:

$$\text{Confidence interval} = \frac{xs}{\sqrt{n}}$$

x=2.23 if n (number of mice)=10 at the risk α=5% x=2.45 if n=6 at the risk α=5% s=the observed mean n=the number of animals per experimental group (10).

A product is considered to be active when the mean diameter of the lesions of the mice treated with this product is equal to or less than the mean diameter of the lesions of the mice treated with N-methylglucamine antimonate (Glucantime®).

The results obtained on BALB/c mice infected with *L. amazonensis* are shown in FIGS. 1 to 4.

FIG. 1(*b*) illustrates the action of alkaloid III in local treatment (a single injection, 14 days after infection, in the infected foot) at a dose of 200 mg/kg (■), compared with that of Glucantime® 400 mg/kg (♦) under the same conditions of treatment; □=controls.

Figure 1A:
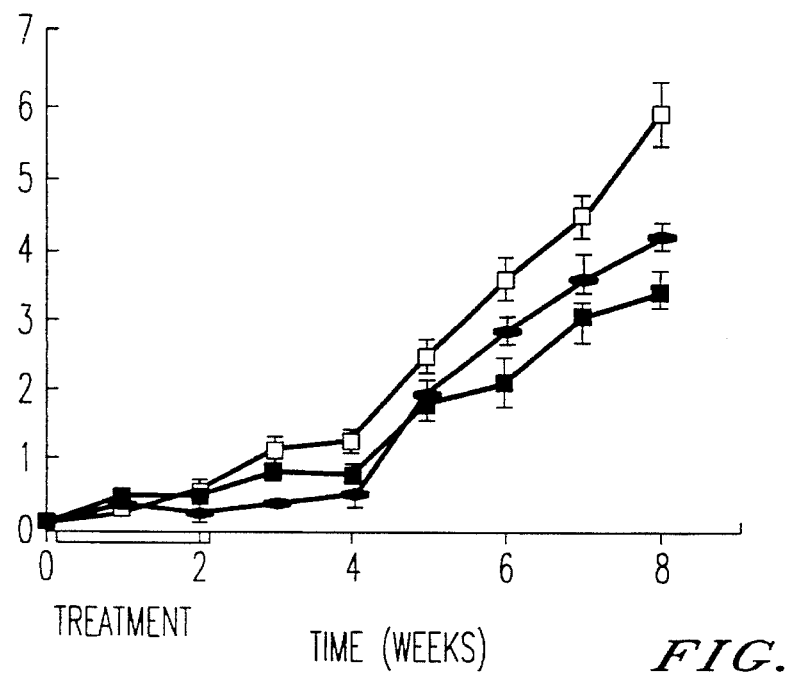
FIG. 1(*a*) illustrates the action of alkaloid III (2-n-propylquinoline) in systemic treatment at a dose of 100 mg/kg/day (■), compared with that of Glucantime (♦) at a dose of 200 mg/kg/day for 14 consecutive days (start of treatment 24 h after infection); □=controls.
Figure 1B:
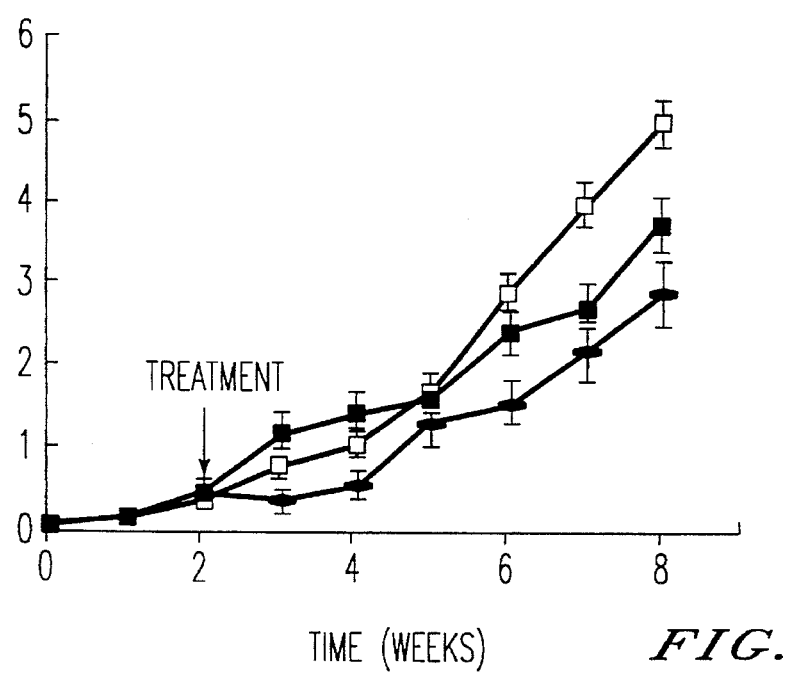
Figure 2:
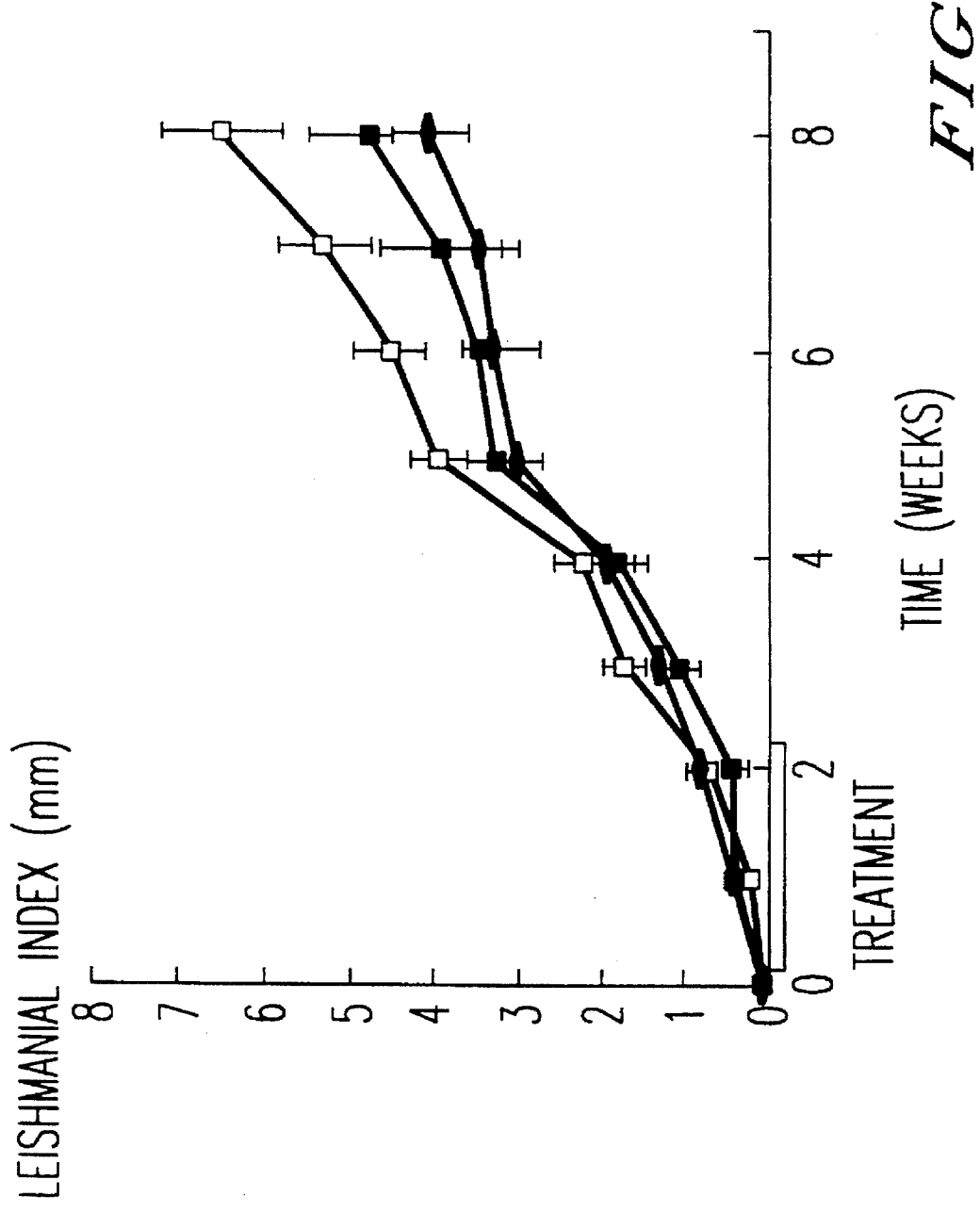
FIG. 2 illustrates the action of alkaloid VII (4-methoxy-2-n-propylquinoline or chimanine A).
Figure 3A:
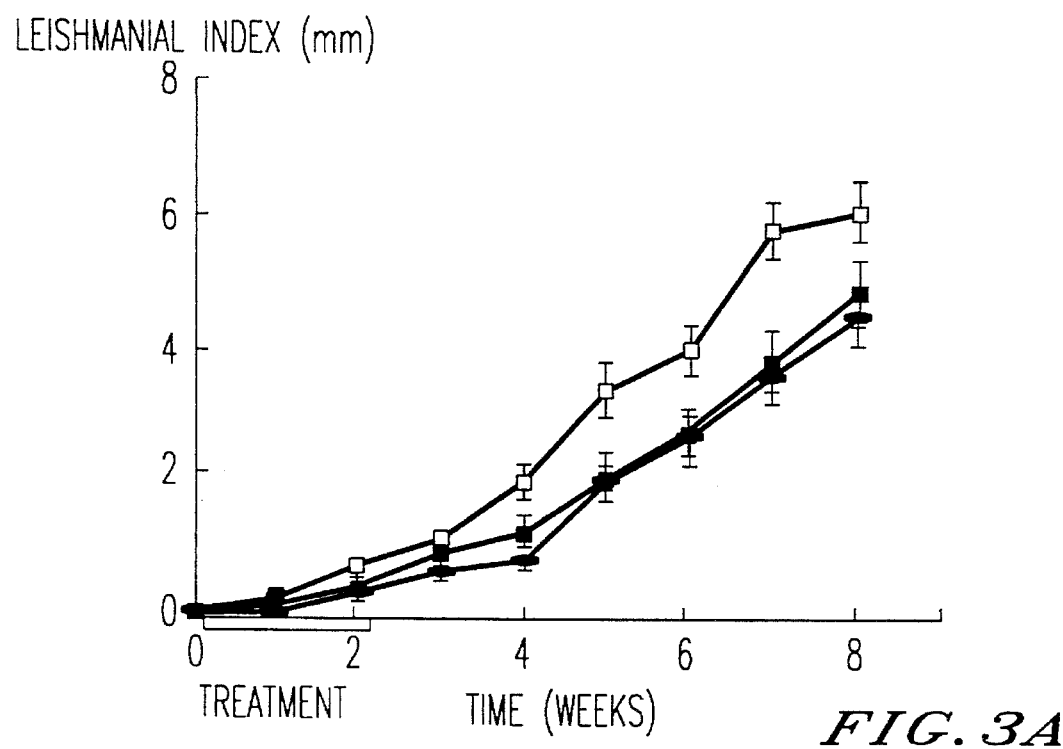
Figure 3B:
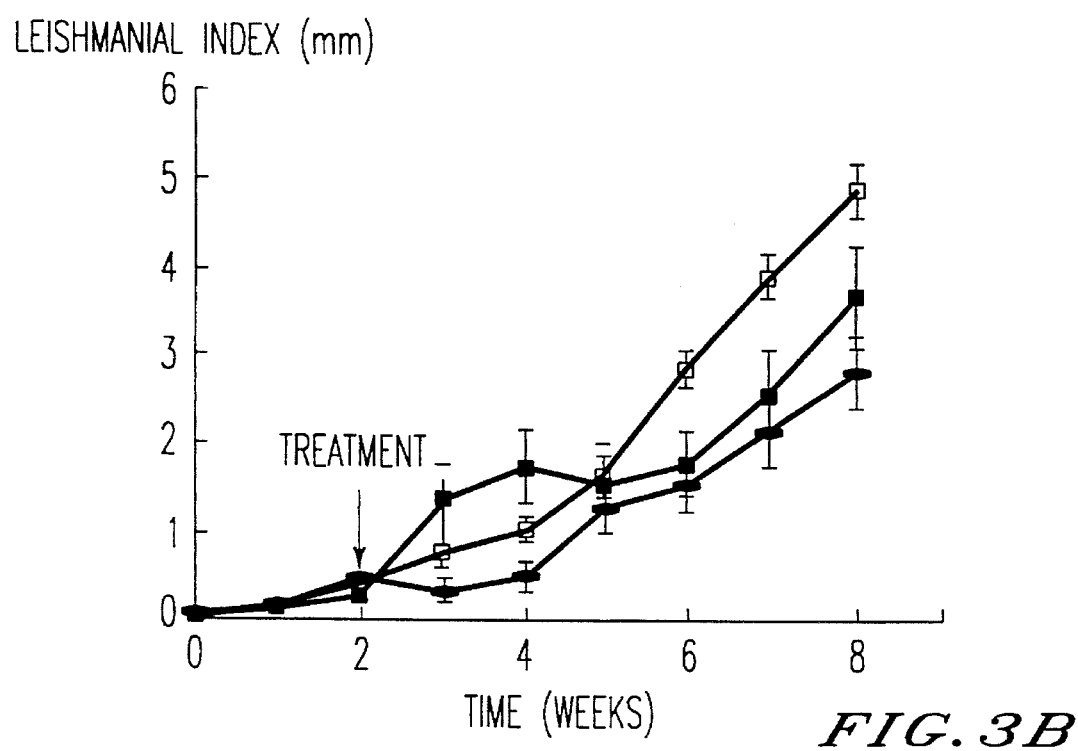
Figure 4:
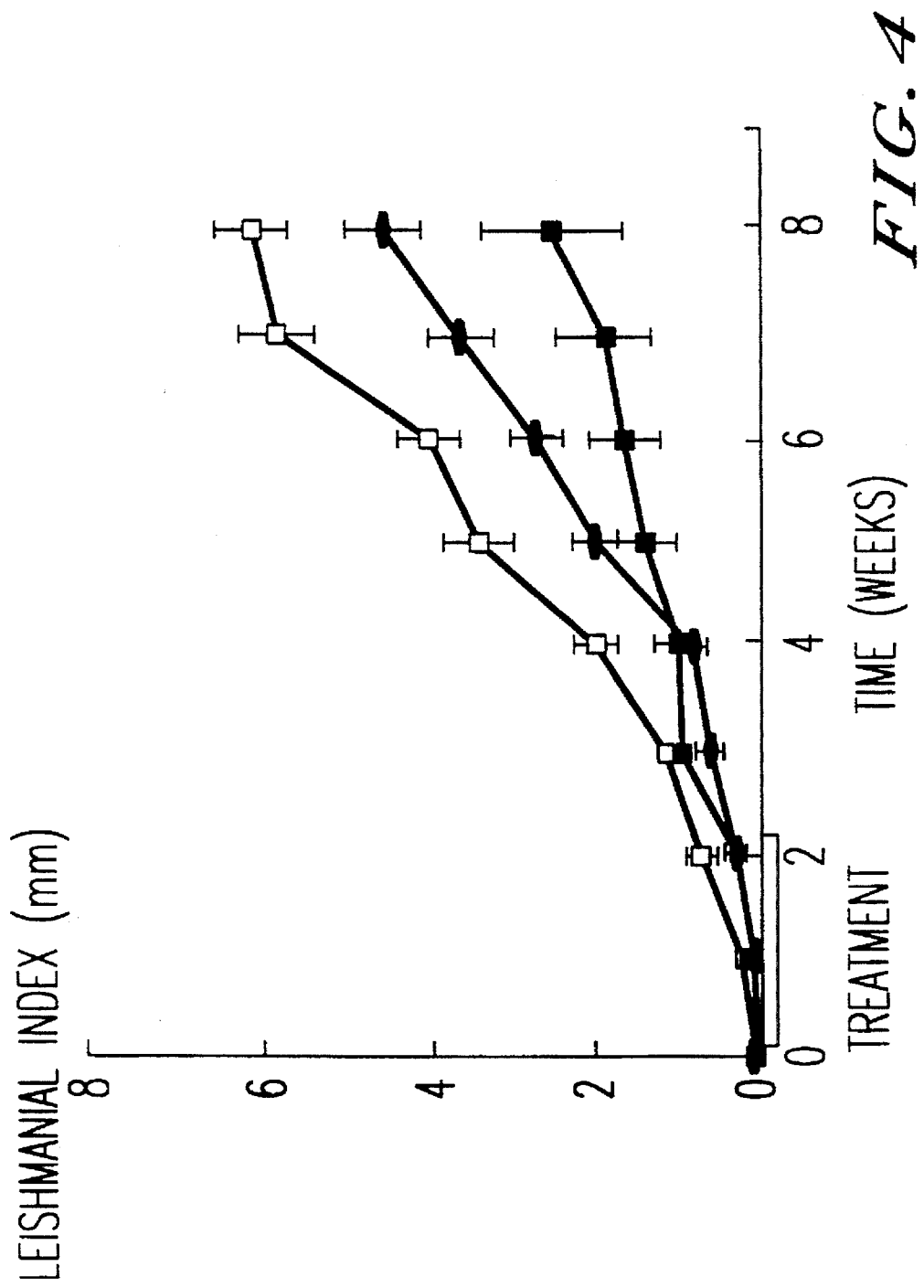

FIGS. 3(*a*) and 3(*b*) illustrate the action of alkaloid XI (2-n-propenylquinoline or chimanine B) in, respectively, systemic treatment at a dose of 100 mg/kg/day (■) compared with that of Glucantime (♦) at a dose of 200 mg/kg/day for 14 consecutive days (start of treatment 24 h after infection); □=controls; and local treatment (a single injection, 14 days after infection, in the infected foot) at a dose of 200 mg/kg (■), compared with that of Glucantime® 400 mg/kg (♦) under the same conditions of treatment.

FIG. IV illustrates the action of alkaloid XII (chimanine D or 2-(1',2'-trans-epoxypropyl)quinoline) in systemic treatment at a dose of 100 mg/kg/day (■), compared with that of Glucantime® (♦) at a dose of 200 mg/kg/day for 14 consecutive days (start of treatment 24 h after infection); □=controls.

EXAMPLE 8

ACTIVITY IN VIVO OF THE ALKALOIDS ACCORDING TO THE INVENTION IN MICE INFECTED WITH LEISHMANIA DONOVANI

1—Experimental protocol

Each group of mice comprises 10 BALB/c mice of the same sex, same weight and same age. Two different protocols were implemented and, for each experiment, several experimental groups were formed;

a) Treatment intraperitoneally an uninfected and untreated control group;

an infected and untreated control group of mice;

a group of mice receiving as treatment the reference product N-methylglucamine antimonate or Glucantime®, on the basis of 0.54 mmol/kg for 5 consecutive days, equivalent to 200 mg/kg;

a group of mice treated with a quinoline at a concentration of 0.54 mmol/kg for 5 consecutive days.

b) Treatment orally or subcutaneously an uninfected and untreated control group;

an infected and untreated control group of mice;

a group of mice receiving as treatment the reference treatment, Glucantime®, on the basis of 0.54 mmol/kg for 5 consecutive days subcutaneously;

a group of mice receiving as treatment Glucantime® on the basis of 0.54 mmol/kg for 10 consecutive days subcutaneously;

a group of mice treated with a quinoline at a concentration of 0.54 mmol/kg for 5 consecutive days subcutaneously;

a group of mice treated with a quinoline at a concentration of 0.54 mmol/kg for 10 consecutive days subcutaneously;

a group of mice treated with a quinoline at a concentration of 0.54 mmol/kg for 5 consecutive days orally;

a group of mice treated with a quinoline at a concentration of 0.54 mmol/kg for 10 consecutive days orally.

2—Mice

Female BALB/c mice weighing 18 g supplied by Iffa-Creddo (France).

3—Infection with *Leishmania donovani*

Mice are infected with amastigotes of *Leishmania donovani* (strain LV/9) via the intracardiac route. This strain is supplied by the Parasitology Laboratory of the London School of Hygiene. The amastigotes are isolated from liver of hamsters infected with *L. donovani* (LV9).

The amount of amastigotes inoculated is $2 \times 10^7$ in 0.2 ml of medium.

4—Treatment with the active principles

The treatments begin one week have parasitic infection and last for 5 days or 10 days.

The active principles (Glucantime® and quinolines) are dissolved under the same conditions as for the in vivo tests described in Example 7. At the end of the experiment, namely 14 days or 21 days after parasitic infection, the mice are sacrificed.

5—Parameters studied

The following parameters are taken into account:

weight gain of the mice (initial weight and autopsy weight);

weight of the liver;

weight of the spleen;

counting under a microscope, on 100 cells originating from application of the liver to a slide, of the number of amastigotes in the cells, and thereafter staining of this slide with May-Giemsa reagent;

percentage reduction in parasitemia relative to infected and untreated control mice.

The results are expressed by calculation of the arithmetic mean, of the variance, of the standard deviation of each parameter and also of Stauber's calculation which takes into account the weight of the liver, and are recorded in Tables I, II and III below.

Table I shows the activity of quinolines administered intraperitoneally in BALB/c mice for 5 consecutive days, one week after infection with *Leishmania donovani* (LV/9), in comparison with Glucantime® administered intraperitoneally.

Table II shows the activity of quinolines administered for 5 days or 10 days subcutaneously to BALB/c mice infected with *Leishmania donovani* (LV 9), compared with that of Glucantime® administered subcutaneously.

Table III shows the activity of a few quinolines administered for 5 days or 10 days orally to BALB/c mice infected with *Leishmania donovani* (LV 9), compared with that of Glucantime® administered subcutaneously.

TABLE I

| Product name | Reduction in parasitemia (%) |
|---|---|
| Glucantime ® | 98 |
| 2-(1',2'-trans-epoxypropyl)quinoline | 57 |
| 2-n-propylquinoline | 62.4 |
| 2-styrylquinoline | 79.6 |
| 2-(2'-hydroxypropyl)quinoline | 55.7 |

TABLE II

| Product name | Treatment period in days | Reduction in parasitemia % | Stauber's calculation |
|---|---|---|---|
| Glucantime | 5 | 90.5 | 89.9 |
| | 10 | 96.9 | 97.4 |
| 2-styrylquinoline | 5 | 43.6 | 37.1 |
| | 10 | 33.3 | 26.3 |
| 2-(1',2'-trans-epoxypropyl)-quinoline | 5 | 69.4 | 69.5 |
| | 10 | 87.4 | 86.6 |
| 2-n-propylquinoline | 5 | 75.9 | 76.3 |
| | 10 | 70.6 | 67.8 |

TABLE III

| Product name | Treatment period in days | Reduction in parasitemia % | Stauber's calculation |
|---|---|---|---|
| Glucantime* | 5 | 90.5 | 89.9 |
| | 10 | 96.9 | 97.4 |
| 2-styrylquinoline | 5 | 34.9 | 42.6 |
| | 10 | 7.8 | 6.1 |
| 2-(1'-2'-trans-epoxypropyl)-quinoline | 5 | 70.6 | 72.9 |
| | 10 | 59.8 | 62.0 |
| 2-n-propylquinoline | 5 | 87.4 | 87.8 |
| | 10 | 70.7 | 99.9 |

*administered subcutaneously

We claim:

1. A method of treating leishmaniasis, comprising:

administering to a subject an effective amount of a purified substituted quinoline compound of the formula (I):

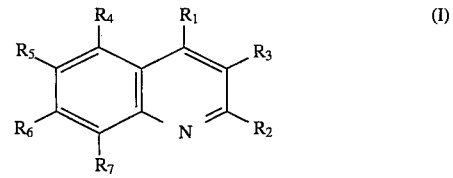

in which $R_1$, $R_3$, $R_4$, $R_6$ and $R_7$ each represent, independently, a hydrogen atom, a linear or branched $C_{1-7}$ alkyl, alkenyl, epoxyalkyl or mono- or polyhydric alcohol group, an amine group or an amide group, a group OR in which R represents hydrogen or a $C_{1-7}$ alkyl or alkenyl group or a phenyl group; and $R_2$ represents:

a group OR in which R has the same meaning as above, or alternatively a $C_{1-7}$ alkyl, alkenyl or epoxyalkyl group, a phenyl group, hydroxyphenyl, methylenedioxyphenyl or dimethoxyphenyl group, or alternatively a $C_{1-7}$ alkyl, alkenyl or epoxyalkyl group bearing at least one of the following substituents: a $C_{1-4}$ alkyl or alkenyl group; a phenyl, phenoxy, dimethylphenyl, dimethoxyphenyl or methylenedioxyphenyl group; or a group OR' in which R' represents hydrogen or a group NHR" in which R" represents hydrogen or a $C_{1-4}$ alkyl or alkenyl group; or an amide group, or alternatively $R_2$ and $R_3$ together form a furan ring; as well as the salts and the derivatives of said quinoline.

2. The method as defined in claim 1, wherein $R_3$, $R_4$ and $R_5$ represent a hydrogen atom and $R_1$, $R_6$ and $R_7$ represent a hydrogen atom or a methoxy group.

3. The method as defined in claim 1, wherein $R_2$ is an ethyl, ethylene or epoxyethyl group bearing at least one of the following substituents:

a $C_4$ alkyl or alkenyl group, or a group OR' in which R' represents hydrogen or a $C_{1-4}$ alkyl or alkenyl group, a phenyl, phenol, dimethylphenyl, dimethoxyphenyl or methylenedioxyphenyl group, an amide or amine group.

4. The method as defined in claim 1, in which:

$R_3$, $R_4$, $R_5$, $R_6$ and $R_7$ are hydrogen atoms;

$R_1$ is a methoxy group;

$R_2$ is a propyl group.

5. The method as defined in claim 1, in which:

$R_1$, $R_3$, $R_4$, $R_5$, $R_6$ and $R_7$ are hydrogen F atoms;

$R_2$ is a trans-epoxypropyl group.

6. The method as defined in claim 1, in which:

$R_1$, $R_3$, $R_4$, $R_5$, $R_6$ and $R_7$ are hydrogen atoms;

$R_2$ is a propyl group.

7. The method as defined in claim 1, in which:

$R_1$, $R_5$, $R_4$, $R_5$, $R_6$ and $R_7$ are hydrogen atoms;

$R_2$ is a propenyl group.

8. A pharmaceutical composition for the treatment of leishmaniasis, which comprises i as active principle, at least one quinoline compound as defined in claims 1 to 7.

9. The pharmaceutical composition for the treatment of leishmaniasis as claimed in claim 8, which is intended for oral administration.

10. A method of treating leishmaniasis, comprising:

administering to a subject an effective amount of a purified substituted quinoline compound of the formula (I):

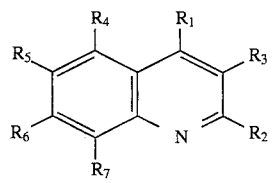

(I)

in which $R_1$, $R_3$, $R_4$, $R_5$, $R_6$ and $R_7$ each represent, independently, a hydrogen atom, a linear or branched $C_{1-7}$ alkyl, alkenyl, epoxyalkyl or mono- or polyhydric alcohol group, an amine group or an amide group, a group OR in which R represents hydrogen or a $C_{1-7}$ alkyl or alkenyl group or a phenyl group; and $R_2$ represents:

a group OR in which R has the same meaning as above, or alternatively a $C_{1-7}$ alkyl, alkenyl or epoxyalkyl group, a phenyl group, phenoxy, methylenedioxyphenyl or dimethoxyphenyl group, or alternatively a $C_{1-7}$ alkyl, alkenyl or epoxyalkyl group bearing at least one of the following substituents: a $C_{1-4}$ alkyl or alkenyl group; a phenyl, phenoxy, dimethylphenyl, dimethoxyphenyl or methylenedioxyphenyl group; or a group OR' in which R' represents hydrogen or a group NHR" in which R" represents hydrogen or a $C_{1-4}$ alkyl or alkenyl group; or an amide group.

11. A pharmaceutical composition for the treatment of leishmaniasis, which comprises, as the active principle, at least one quinoline as defined in claim 10.

12. The pharmaceutical composition for the treatment of leishmaniasis as claimed in claim 11, which is intended for oral administration.

13. A method of treating leishmaniasis, comprising:

administering to a subject an effective amount of a purified substituted quinoline compound of the formula (I):

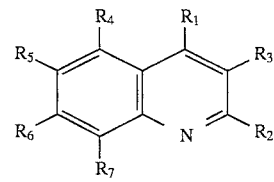

in which $R_1$, $R_3$, $R_4$, $R_5$, $R_6$ and $R_7$ each represent, independently, a hydrogen atom, a linear or branched $C_{1-7}$ alkyl, alkenyl, epoxyalkyl or mono- or polyhydric alcohol group, an amine group or an amide group, a group OR in which R represents hydrogen or a $C_{1-7}$ alkyl or alkenyl group or a phenyl group; and $R_2$ represents:

a group OR in which R has the same meaning as above, or alternatively a $C_1$ or $C_7$ alkyl, alkenyl or epoxyalkyl group, a phenyl group, hydroxyphenyl, methylenedioxyphenyl or dimethoxyphenyl group, or alternatively a $C_{1-7}$ alkyl, alkenyl or epoxyalkyl group bearing at least one of the following substituents: a $C_{1-4}$ alkyl or alkenyl group; a phenyl, hydroxyphenyl, dimethylphenyl, dimethoxyphenyl or methylenedioxyphenyl group; or a group OR' in which R' represents hydrogen or a group NHR" in which R" represents hydrogen or a $C_{1-4}$ alkyl or alkenyl group; or an amide group, or alternatively $R_2$ and $R_3$ together form a furan ring; as well as the salts and the derivatives of said quinoline with the proviso:

(1) when $R_1$, $R_3$ and $R_4$ to $R_7$ are hydrogen, $R_2$ cannot be phenyl, methylenedioxyphenyl or dimethoxyphenyl; and (2) when $R_3$ and $R_4$–$R_7$ are hydrogen and $R_1$ is methoxy, $R_2$ cannot be methylenedioxyphenylethenyl, pentyl, pentenyl, methylenedioxy phenylethyl or phenyl.

14. A method of treating leishmaniasis comprising:

administering to a subject and effective amount of purified 4-methoxy-2-n-propylquinoline, 2-(1',2'-trans-epoxypropyl)quinoline, 2-n-propyl-quinoline and 2propylquinoline.

* * * * *